(12) United States Patent
Tiedtke

(10) Patent No.: US 8,918,186 B2
(45) Date of Patent: Dec. 23, 2014

(54) DEVICE WITH FLEXIBLE MULTILAYER SYSTEM FOR CONTACTING OR ELECTROSTIMULATION OF LIVING TISSUE CELLS OR NERVES

(75) Inventor: Hans-Jürgen Tiedtke, Bonn (DE)

(73) Assignee: Pixium Vision SA, Paris (FR)

( * ) Notice: Subject to any disclaimer, the term of this patent is extended or adjusted under 35 U.S.C. 154(b) by 243 days.

(21) Appl. No.: 12/280,123

(22) PCT Filed: Jan. 26, 2007

(86) PCT No.: PCT/EP2007/000685
§ 371 (c)(1),
(2), (4) Date: Jan. 20, 2009

(87) PCT Pub. No.: WO2007/101508
PCT Pub. Date: Sep. 13, 2007

(65) Prior Publication Data
US 2009/0228085 A1 Sep. 10, 2009

(30) Foreign Application Priority Data
Feb. 21, 2006 (DE) .......................... 10 2006 008 050

(51) Int. Cl.
*A61N 1/05* (2006.01)
*A61N 1/40* (2006.01)
(52) U.S. Cl.
CPC ................. *A61N 1/40* (2013.01); *A61N 1/0541* (2013.01); *A61N 1/0543* (2013.01)
USPC ........................................... 607/116; 607/117
(58) Field of Classification Search
CPC .. A61N 1/0543; A61N 1/0531; A61N 1/0551
USPC .................................................. 607/116–117
See application file for complete search history.

(56) References Cited

U.S. PATENT DOCUMENTS

| 4,926,879 | A |   | 5/1990  | Sevrain et al. |
|-----------|---|---|---------|----------------|
| 4,969,468 | A | * | 11/1990 | Byers et al. ................... 600/373 |
| 5,505,201 | A |   | 4/1996  | Grill, Jr. et al. |
| 5,750,926 | A |   | 5/1998  | Schulman et al. |
| 6,052,608 | A |   | 4/2000  | Young et al. |

(Continued)

FOREIGN PATENT DOCUMENTS

| DE | 197 50 043 A1 | 5/1999 |
|----|---------------|--------|
| JP | 10242324      | 9/1998 |

(Continued)

OTHER PUBLICATIONS

International Search Report and Written Opinion for International Application No. PCT/EP2007/000685; mailed Apr. 18, 2007; 8 pages.

(Continued)

*Primary Examiner* — Joseph Stoklosa
(74) *Attorney, Agent, or Firm* — Workman Nydegger

(57) ABSTRACT

The object,—to create a printed circuit board for an implant having improved properties in connection with the electrical contacting via the contact points of the conductor tracks on the printed circuit board,—is achieved, according to the present invention, by means of a device for contacting and/or electrostimulation of living tissue cells or nerves with having a printed circuit board having with at least one contact point for electrical contacting, the printed circuit board encompassing comprising a flexible multilayer system with at least one conductor track. In accordance with the invention, the contact points for the conductor track in the multilayer system are galvanically reinforced. To this end, a galvanically reinforced layer is grown onto the already preprocessed contact point, for example by means of a galvanic process. By virtue of the application of one or more additional material layers onto the contact points of the conductor tracks, these latter are mechanically more stably anchored in the printed circuit board in mechanically more stable manner and hence become more reliable in their function.

21 Claims, 3 Drawing Sheets

(56) References Cited

U.S. PATENT DOCUMENTS

| | | | |
|---|---|---|---|
| 6,477,034 B1 * | 11/2002 | Chakravorty et al. | 361/306.3 |
| 6,633,081 B2 | 10/2003 | Sahara et al. | |
| 6,861,744 B2 | 3/2005 | Hayama et al. | |
| 6,974,533 B2 | 12/2005 | Zhou | |
| 8,180,460 B2 * | 5/2012 | Nevsmith et al. | 607/116 |
| 8,554,340 B2 * | 10/2013 | Janik et al. | 607/116 |
| 2002/0108781 A1 * | 8/2002 | Mune et al. | 174/264 |
| 2003/0195601 A1 * | 10/2003 | Hung et al. | 607/116 |
| 2004/0021022 A1 | 2/2004 | Amano et al. | |
| 2004/0082875 A1 | 4/2004 | Donoghue et al. | |
| 2004/0094841 A1 | 5/2004 | Matsuzaki et al. | |
| 2004/0210122 A1 | 10/2004 | Sieburg | |
| 2005/0085009 A1 | 4/2005 | Yamaguchi | |
| 2005/0137670 A1 | 6/2005 | Christopherson et al. | |
| 2005/0173809 A1 | 8/2005 | Yamamoto et al. | |
| 2006/0003090 A1 | 1/2006 | Rodger et al. | |

FOREIGN PATENT DOCUMENTS

| | | |
|---|---|---|
| JP | 2001/215207 | 8/2001 |
| JP | 2004/195206 | 7/2004 |
| JP | 05-075259 | 3/2005 |
| JP | 2005279000 | 10/2005 |
| WO | WO 95/31145 | 11/1995 |
| WO | WO 99/24109 | 5/1999 |
| WO | WO 99/49933 | 10/1999 |

OTHER PUBLICATIONS

Agnew William et al, Neural Prosthesis: Fundamental Studies, Prentice Hall, 1990.

Feltham A. et al, Platinized platinum electrodes, Chemical Reviews, 1971.

Gross M. et al, Micromachining of flexible neural implants with low-ohmic wire traces using electroplanting, Sensors and Actuators A, 2002.

Robblee Lois et al, Electrochemical guidelines for selection of protocols and electrode materials for neural stimulation, Prentice Hall, 1990.

Sieglitz T. et al, A biohybrid system to interface peripheral nerves after traumatic lesions: design of a high channel sieve electrode, Biosensors and Bioelectronics, 2002.

* cited by examiner

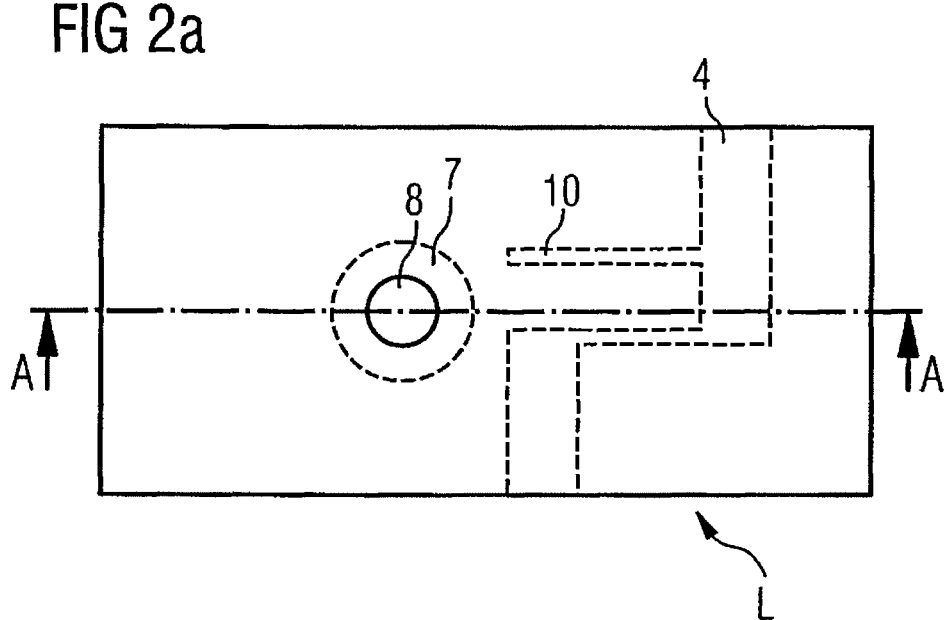
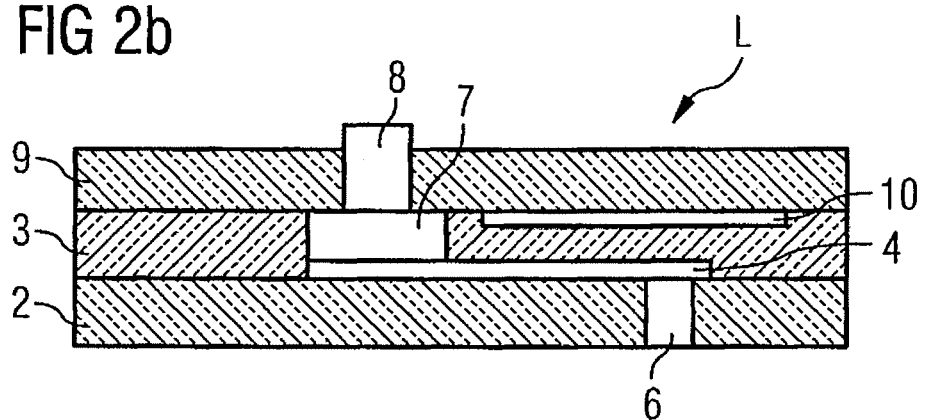

DEVICE WITH FLEXIBLE MULTILAYER SYSTEM FOR CONTACTING OR ELECTROSTIMULATION OF LIVING TISSUE CELLS OR NERVES

This application is the U.S. National Stage of PCT/EP 2007/000685, filed on Jan. 26, 2007, which claims priority to DE 10 2006 008 050.5, filed on Feb. 21, 2006, both of which are incorporated herein by reference in their entirety.

The present invention relates generally to systems that serve for contacting living tissue or nerves. The invention relates to a device for contacting or electrostimulation of living tissue cells or nerves with a printed circuit board encompassing at least one contact point for electrical contacting of implants with multilayer systems with printed circuit boards in which at least one contact pad of a flexible printed circuit board is positively anchored in the printed circuit board, wherein a mechanical reinforcement of the contact pad being is achieved by galvanic growth of conductor-track material.

Devices are known in the form of implants for stimulating living tissue, such as, for example, implants for the retina of the human eye or for the human inner ear. As a rule, such implants encompass a number of stimulating electrodes, via which electrical stimulating pulses are delivered to the surrounding tissue or to the cells, in order in this way to stimulate the nerves and hence thereby to re-establish or to improve their function thereof.

Known implants are frequently an integral part of systems that encompass electrical or electronic components for diagnostic purposes such as, for example, the electrical measurement of bodily functions, blood pressure, blood sugar or temperature. Such systems may also include glucose sensorics, ultrasound sensorics, components for image-recording or for sound-recording and, in particular, components for actoric purposes. With such systems it may also be a question of stimulation systems that include componentsfor actoric purposes such as, for example, for electrostimulation, defibrillation, emission of sound or emission of ultrasound. As a rule, such systems encompass comprise a substrate in the form of a printed circuit board on which the electronic modules components are arranged, with electrical contacts that are in direct or indirect contact with the body tissue such as, for example, nerve tissue and muscle tissue, or with body fluids such as blood, for example, blood.

In order to keep the dimensions of the electrical or electronic components as small as possible, besides ceramic substrates, flexible printed printed circuit boards made of plastics,—for example, polyimide, parylenes,—are also being increasingly employed. Such flexible printed printed circuit boards can are able to be structured in very fine dimensions with a layer thickness of the conductor track from a few nanometres up to a few hundred nanometres and with a conductor-track width of, for example, a few micrometres with the aid of established processes for producing microchips having very fine dimensions with a layer thickness of the conductor track from a few nanometres up to a few hundred nanometres and with a conductor-track width of, for example, a few micrometres.

As a rule, such a flexible printed circuit board consists of one or more insulating layers, for example made of polyimide, parylenes or other plastics, insulators or flexible semiconductors, on which conductor tracks, contact areas or, where appropriate, through-connections metallised holes between several multiple conductor-track planes have been established. For the electrical contacting of the conductor tracks, corresponding contact points or contact pads are provided, via which electrical leads and/or modules can, for example, can be attached, in order to connect the electronic components on the printed circuit board to external components of the stimulation system.

With these flexible printed circuit boards, however, there exists the problem that the thin conductor tracks are mechanically extremely sensitive, particularly at their contact points, which can result in loss of the electrical contact with the contact points and the conductor tracks. A further problem of these contact points or contact pads consists in the anchorage within the very thin, flexible printed circuit board for the implant. As a rule, the conductor track has a thickness from a few nanometres up to a few hundred nanometres, and the insulating layer has a thickness of a few micrometres. Critical in this regard is the fact that the contact point is only insufficiently anchored mechanically in the conductor track. In particular, as a result of mechanical loads in the course of the manufacturing, inserting of components assembly, or processing of the printed circuit boards for an implant, a contact pad can be easily dissolved loosened out of from the flexible printed circuit board by reason of mechanical compressive force, tensile force, shear force, flexural stress, expansion, vibration by ultrasound etc.

It is therefore an object of the present invention to create a printed circuit board for an implant having improved properties in connection with the electrical contacting via the contact points of the conductor tracks on the printed circuit board.

This object is achieved by means of the device according to the invention having the features according to claim 1. Advantageous further developments of the invention are specified in each of the dependent claims.

According to one aspect of the present invention, the aforementioned object is achieved by means of a device for contacting and/or electrostimulation of living tissue cells or nerves with a printed circuit board that encompasses at least one electrically insulating material layer on which a conductor-track layer with at least one conductor track is arranged. For the electrical contacting of the conductor track, at least one contact point is provided. Above the conductor track at least one additional material layer is arranged, through which the contact point extends. In this way, the conductor track is electrically contactable from outside of the printed circuit board through the additional material layer via the contact point.

According to a further aspect of the present invention, the aforementioned object is achieved by means of a process method for producing a printed circuit board in the form of a multilayer system for a device for contacting and/or electrostimulation of living tissue cells or nerves, said process comprising the following steps:

generating a first insulating material layer,
generating a conductor track on the first insulating material layer,
generating a second insulating material layer,
generating at least one window in the second insulating material layer,
filling the window in the second insulating material layer with an electrically conducting material for to the purpose of generating a contact point that exhibits an electrical contact with the conductor track
generating an additional insulating material layer on the second insulating material layer,
generating at least one window in the additional insulating material layer, the window in the additional insulating material layer exhibiting smaller lateral dimensions than the window in the second insulating material layer, filling the window in the additional insulating material layer with an electrically conducting material for to the purpose of generating a contact pad that exhibits an electrical contact with the contact point.

Consequently, with the process method according to the invention the contact points for the conductor tracks of the implant,--such as, for example, a stimulating electrode,--are reinforced by means of one or more additional material layers. In this connection, a galvanically reinforced layer is grown onto the already preprocessed contact point, for example by means of a galvanic process. Alternatively, besides the galvanic application of metal, other suitable processes for applying one or more material layers may also be employed, such as sputtering, for example. Through the subsequent application of one or more additional material layers onto the prestructured contact points of the conductor tracks, these latter are mechanically more stably integrated within the printed circuit board in a mechanically more stable manner and hence become more reliable in their function,--i.e. the contact points can be contacted more reliably, and the electrical contact better can be maintained better, and the contact points are anchored better in the stimulating electrode.

According to a preferred embodiment of the present invention, the flexible printed circuit board for an implant consists of multiple layers of an insulating material with conductor tracks, arranged in-between, said layers, or underneath, them, or on top of them, which conductor tracks are mechanically reinforced prior to the application of further surface layers of insulating material in the region of the contact points prior to the application of further surface layers of insulating material. The application of one or more mechanically reinforcing layers on the printed circuit board is effected, for example, by means of galvanic processes, by means of sputtering or by other suitable processes. Alternatively, or in addition, appropriate contact pads made of metal may are also able to be fastened to the contact points. This is preferably done by gluing them on with the aid of a conductive adhesive, by soldering, welding, ultrasonic bonding, thermocompression bonding, crimping pressing on or clipping.

The manufacture of the fine structures of a flexible printed circuit board that is suitable for use in an implant is carried out, as a rule, with the aid of lithographic processes that are already established for the production of semiconductors from silicon wafers.

With this process method, it is possible for galvanically reinforced and positively anchored contact pads to be generated with positive anchorage in flexible printed circuit boards, which can be used in devices with a flexible multilayer system for contacting or electrostimulation of living tissue cells or nerves. The contact pads may be fitted optionally on the upper side and/or on the underside of the printed circuit board of the flexible multilayer system. Instead of, or together with, the contact pads, electrodes for electrostimulation of living tissue or nerves can also be established or arranged in the flexible printed circuit board. Via through-metallised holes connections through the insulating material layers of the flexible printed circuit board, it is possible for electrical contacts from the contact pads or from the contact points to the inner metal conductor tracks of the multilayer system are able to be produced.

A further special feature of the process method for producing a printed circuit board according to the present invention that is suitable for use in an implant consists in the fact that, on the one hand, a galvanic manufacturing process is employed in order to achieve mechanical reinforcements of the contact pads or at the contact points, and that these galvanically reinforced contact points are positively anchored in the printed circuit board by means of internal electroplating layers; this means that the internal inner electroplating layer of the contact pad in question is larger in its lateral dimensions than the external outer electroplating layer of the contact pad, so that a good mechanical anchorage is obtained in relation to mechanical forces acting from outside. This good mechanical anchorage of the contact pad(s) in the printed circuit board is an important prerequisite for mechanical interconnection techniques to be carried out subsequently, such as, for example, ultrasonic bonding, conductive bonding, thermocompression bonding, flip-chip bonding and other electrical interconnection processes.

A good mechanical anchorage of the contact pad in the printed circuit board for an implant is also a prerequisite for the production of mechanically robust electrodes on the flexible printed circuit board, this being which is of great importance in neuroprosthetics, for example. Such electrodes can be used, in particular, for electrostimulatory purposes, for example in a retinal implant, in a cochlear implant, for brainstem stimulators, deep-brain stimulations, spinal-cord stimulators or other stimulators. On the other hand, there is also the possibility also exists of realising bleeder recording electrodes with the described process method, which may, which, for example, can be used for electrophysiological measurements of neural activity or of the impedance of biological or chemical systems.

Further particulars, preferred embodiments and advantages of the present invention will become apparent from the following description with reference to the appended drawings. Shown are:

FIG. 2a illustrates a schematic representation of the structure of a printed circuit board according to a second preferred embodiment of the present invention for use in a device for contacting or electrostimulation of living tissue cells or nerves;

FIG. 2b illustrates a schematic sectional representation of the embodiment of the printed circuit board according to the invention that is shown in FIG. 2a.

Figure 3A:
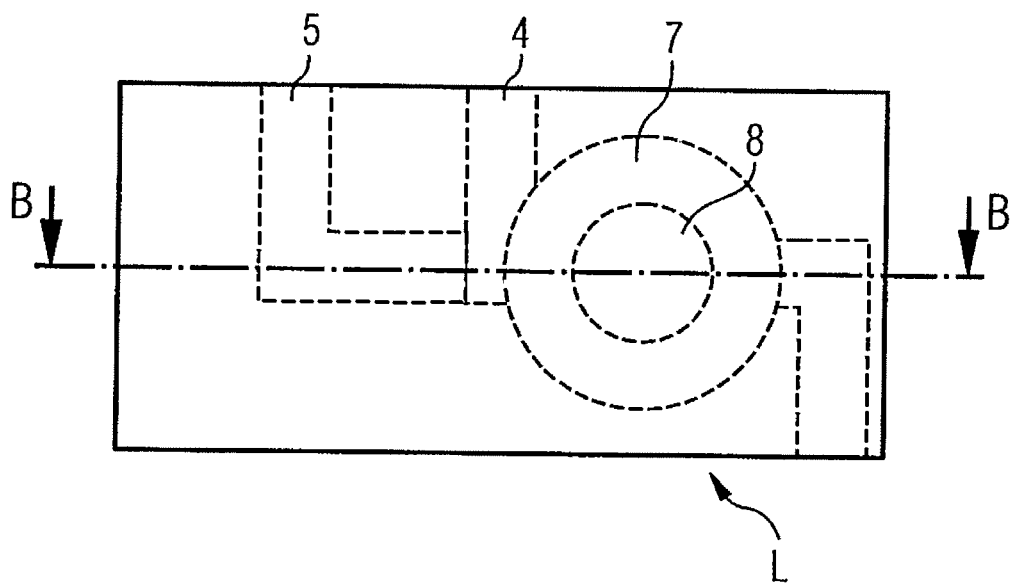
Figure 3B:
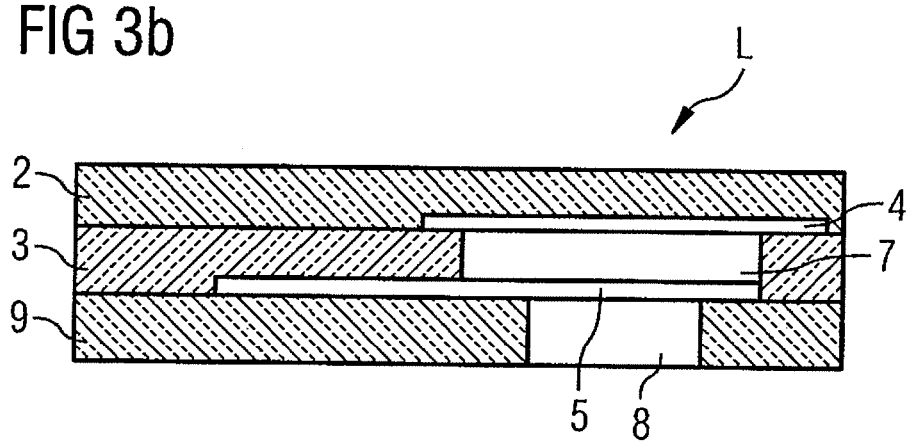

FIG. 3a illustrates a schematic representation of the structure of a printed circuit board according to a third preferred embodiment of the present invention for use in a device for contacting or electrostimulation of living tissue cells or nerves; and FIG. 3b illustrates a schematic sectional representation of the embodiment of the printed circuit board according to the invention that is shown in FIG. 3a.

Figure 1:
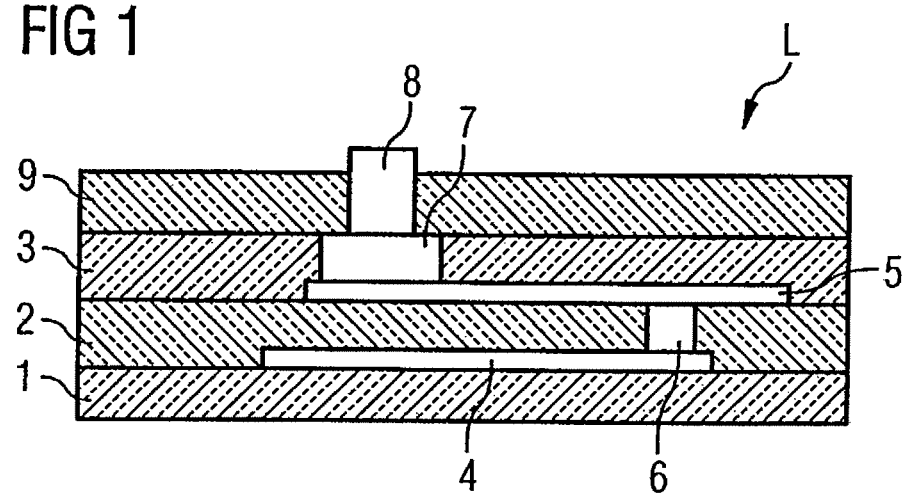
FIG. 1 illustrates a schematic representation of the structure of a printed circuit board according to a first preferred embodiment of the present invention for use in a device for contacting or electrostimulation of living tissue cells or nerves.

FIG. 1 is a schematic representation of the structure of a printed circuit board L according to a first preferred embodiment of the present invention for use in a device for contacting or electrostimulation of living tissue cells or nerves.

The printed circuit board L represented in FIG. 1 encompasses comprises three material layers 1, 2, 3 made of an electrically insulating material such as, for example, polyimide, parylenes or another insulator. On these insulating layers 1, 2, 3 a lower conductor track 4 and an upper conductor track 5 are formed. The conductor tracks 4 and 5 are each situated lie in a corresponding conductor-track plane, whereby the conductor-track plane of conductor track 4 being is located between the insulating material layer 1 and the insulating material layer 2, and the conductor-track plane of conductor track 5 being lies situated between the insulating material layer 2 and the insulating material layer 3. In the case of the embodiment of the printed circuit board L according to the invention that is represented in FIG. 1, the conductor tracks 4 and 5 are electrically connected to one another via a through-metallised hole connection 6 between the conductor-track planes.

The upper conductor track 5 is furthermore provided with a contact area and/or a contact point 7 which extends from the conductor-track plane of the upper conductor track 5 as far as to the outer edge of the printed circuit board L. For the electrical contacting of the conductor tracks, contact points 7 are provided, to which external electrical leads can be attached in order to connect the electronic components on the printed circuit board L to with further electrical components of a system. An electrode 8 may also be applied onto the contact point 7. The conductor tracks 4, 5 may be constructed, for example, from titanium, copper, gold, silver, platinum, conductive plastic or other electrically conductive materials. The printed circuit board L according to the invention can be produced by processes for generating microstructures such as are known, for example, from the production of semiconductor modules. With the aid of such processes, very fine dimensions of the printed circuit board L can be achieved, whereby the layer thickness of the conductor tracks 4, 5 may amount to from a few nanometres up to a few hundred nanometres and the layer thickness of the insulating material layers 1, 2, 3 may amount to a few micrometres.

In order to achieve the aforementioned object of a mechanically more stable and functionally more reliable arrangement of the contact points 7 or electrode pads 8 in the printed circuit board L, according to the present invention the contact points 7 for the conductor tracks 5 are subsequently reinforced by means of one or more additional material layers 9. In the case of the first embodiment of the printed circuit board L according to the invention that is represented in FIG. 1, a layer 9 made of electrically insulating material is arranged on the contact point 7 of the printed circuit board L. Through the arrangement of one or more additional material layers 9 on the contact point 7 of the conductor track 5, the contact point 7 is mechanically more stably anchored in the printed circuit board L in a mechanically more stable manner and hence can be contacted more reliably.

Arranged on the contact point 7 is a contact pad 8 made of an electrically conductive material which extends through the additional material layer 9, via which pad the contact point 7 can be contacted from outside. This is preferably done by sputtering, galvanic growth, gluing on with the aid of a conductive adhesive, by soldering, welding, ultrasonic bonding, thermocompression bonding, crimping pressing or clipping. Several Multiple additional material layers 9 may also be arranged on the material layer 3 above the conductor-track plane with the upper conductor track 5. The contact pad 8 made of electrically conducting material is then formed in such a way that it extends from the contact point 7 through all the additional material layers 9, in order to be able to contact the contact point 7 electrically from outside of the conductor tracks. In this way, galvanically reinforced and positively anchored contact pads 8 or even electrodes can be established both on the upper side and on the underside of the printed circuit board L, which via respective contact points 7 enable an electrical contact with the inner metallic conductor tracks 4 and 5 of the printed circuit board L.

FIG. 2a shows a schematic representation of the structure of a printed circuit board L according to a second preferred embodiment of the present invention with a contact point 7, and contact pad 8 formed on the upper side of the printed circuit board L, and FIG. 2b shows a schematic sectional representation of the embodiment of the printed circuit board L according to the invention that is shown in FIG. 2a. The embodiment of a printed circuit board L according to the invention that is shown therein again encompasses comprises three insulating material layers 2, 3 and 9, as well as two conductor-track layers with electrically conducting conductor tracks 4 and 10. The lower conductor track 4 is situated between the insulating material layers 2 and 3, whereas the upper conductor track 10 is arranged between the insulating material layers 3 and 9.

The lower conductor track 4 is electrically contacted via a through-metallised hole connection 6, and the lower conductor track 4 is equipped with a contact point 7 on which a contact pad or electrode pad 8 is arranged. Both the through-connection metallised hole 6 and as well as the contact point 7 and the contact pad 8 are designed constructed in the form of an electroplating layer,—i.e. they have been generated as a galvanic metallic coating by a galvanic process. Above the upper conductor track 10 an additional insulator layer 9 is arranged which is situated above the contact point 7 and includes within itself incorporates the contact pad 8 within it. Consequently, through the use of galvanic processes a reinforcement of the contact point 7 or of the contact pad 8 is achieved, and through the application of the additional material layer 9 on the upper conductor-track layer opposite the insulating material layer 3 a positive anchorage of the contact point 7, 8 on the upper side of the printed circuit board L is achieved.

The contact pad 8 extends from the contact point 7 as far as the upper edge, or beyond it, of the additional material layer 9, so that the conductor track 4 is electrically contactable from outside of the printed circuit board L. As a result, the contact point 7 encompasses comprises a lower part and an upper part, whereby the lower part exhibits a larger lateral dimension than the upper part. In this way, the contact point 7, and the contact pad 8 is anchored better in the printed circuit board L and is less sensitive to mechanical deformations and/or tensile forces perpendicular to the flexible printed circuit board L.

FIG. 3a shows a schematic representation of the structure of a printed circuit board L according to a third preferred embodiment of the present invention, with a contact point 7, and contact pad 8 formed on the underside of the printed circuit board L, and FIG. 3b shows a schematic sectional representation of the embodiment of the printed circuit board L according to the invention that is shown in FIG. 3a. The embodiment, shown therein, of a printed circuit board L according to the invention has, in part, a similar structure to that of the embodiment shown in FIGS. 2a and 2b.

The embodiment of a printed circuit board L according to the invention that is shown in FIGS. 3a and 3b exhibits a contact point 7, and a contact pad 8 on the underside and again encompasses comprises three insulating material layers 2, 3 and 9, as well as two conductor-track layers with electrically conducting conductor tracks 4 and 5. The upper conductor track 4 lies situated between the insulating material layers 2 and 3, whereas the lower conductor track 5 is arranged between the insulating material layers 3 and 9.

The upper conductor track 4 is electrically contacted via a contact point 7, and the lower conductor track 5 is electrically contacted via a contact pad 8. The contact point 7 and the contact pad 8 have again been generated by a galvanic process. Below the lower conductor track 5 an additional insulating material layer 9 is arranged which lies situated below the contact point 7 and encompasses loses the contact pad 8. The contact pad 8 extends from the contact point 7 as far as the lower edge, or beyond it, of the additional material layer 9, so that the conductor track 4 is electrically contactable from outside of the printed circuit board L. In this way, the contact point again consists of a first part 7 which exhibits a larger lateral dimension than the second part 8 and is, as a result, reliably anchored in the printed circuit board L.

List of Reference Symbols

1 insulating material layer or insulator layer
2 insulating material layer or insulator layer
3 insulating material layer or insulator layer
4 conductor track or conductor-track plane
5 conductor track or conductor-track plane
6 through-connectionmetallised hole
7 lower part of the contact point
8 upper part of the contact point or contact pad
9 insulating material layer or insulator layer
10 conductor track or conductor-track plane
A sectional plane of the representation in FIG. 2*b*
B sectional plane of the representation in FIG. 3*b*
L printed circuit board

The invention claimed is:

1. A device for contacting and/or electrostimulation of living tissue cells or nerves, the device comprising:
a flexible circuit board including at least one contact point, the flexible circuit board including the following layers:
at least one electrically insulating material layer and at least one conductor-track layer having a conductor track, the at least one electrically insulating material layer formed over the at least one conductor-track layer; and
at least one additional insulating material layer, the at least one additional insulating material layer formed over the at least one electrically insulating material layer and arranged on a portion of the contact point, the at least one additional insulating material layer configured to reinforce the contact point in the circuit board, wherein the conductor track is electrically contactable from outside of the circuit board through the additional insulating material layer via the contact point,
wherein the at least one contact point includes:
a first part that is in direct contact with one of the at least one conductor-track layer, and
a second part that is in contact with the at least one additional insulating material layer, wherein the first and second parts of the at least one contact point extend parallel to each other, wherein the first part has larger lateral dimensions than the second part, and wherein the second part is provided in the form of a contact pad.

2. The device according to claim 1, wherein the first part of the contact point is at least partially overlapped by the additional material layer, and the second part of the contact point is at least partially surrounded by the additional material layer.

3. The device according to claim 1, wherein the at least one additional insulating material layer includes more than one additional insulating material layer, wherein the contact point extends from the conductor track through the at least one additional insulating material layer as far as an outer edge of the circuit board.

4. The device according to claim 1, wherein the conductor track is applied on one of the electrically insulating material layers.

5. The device according to claim 1, wherein the conductor track is integrated within one of the electrically insulating material layers.

6. The device according to claim 1, wherein the conductor track is arranged between two electrically insulating material layers.

7. The device according to claim 1, wherein the at least one conductor-track layer includes several conductor tracks which are substantially separated from one another by at least one of the at least one insulating material layer.

8. The device according to claim 1, wherein the at least one conductor-track layer includes several conductor tracks which are electrically connected to one another via through-connections or via electroplating layers.

9. The device according to claim 1, wherein the conductor-track layers are arranged parallel to one another.

10. The device according to claim 1, wherein the thickness of the conductor-track layers lies within the range between a few nanometres up to a few hundred nanometres and the layer thickness of the insulating material layers lies within the range of a few micrometres.

11. The device according to claim 1, wherein the conductor-track layers and the insulating material layers are arranged parallel to one another.

12. The device according to claim 1, wherein the contact point is configured for electrically contacting the conductor track and is arranged on the upper side and/or on the underside of the circuit board.

13. The device according to claim 1, wherein the contact point is configured for electrically contacting the conductor track and wherein the second part includes a contact pad or electrode pad which is electrically contactable from outside of the circuit board.

14. The device according to claim 13, wherein the contact point or the contact pad extends at least as far as an outer edge of the circuit board or projects beyond it.

15. The device according to claim 13, wherein the contact point and/or the contact pad is/are integrated within the additional material layer.

16. A system for electrically contacting and/or electrostimulation of living tissue or nerves via one or more electrodes having a device according to claim 1.

17. The device according to claim 14, wherein the contact point and/or the contact pad is/are integrated within the additional material layer.

18. The device according to claim 1, wherein the first part is disposed in or in direct contact with the at least one electrically insulating material layer.

19. The device according to claim 1, wherein the first part is in direct contact with the at least one additional insulating material layer, and wherein the first part is incorporated into the at least one electrically insulating material layer.

20. The device according to claim 1, wherein the second part is formed in the at least one additional insulating material layer.

21. A device for contacting and/or electrostimulation of living tissue cells or nerves, the device comprising:
a flexible circuit board including at least one contact point that includes a first part and a second part, the flexible circuit board including the following layers:
at least one electrically insulating material layer and at least one conductor-track layer having a conductor track, the at least one electrically insulating material layer formed over the at least one conductor-track layer; and
at least one additional insulating material layer formed over the at least one electrically insulating material layer and the first part, the at least one additional insulating material layer configured to reinforce the contact point in the circuit board, wherein the conductor track is electrically contactable from outside of the circuit board through the additional insulating material layer via the contact point, wherein:
- the first part is in direct contact with one of the at least one conductor-track layer, wherein the first part of the contact point is at least partially overlapped by the additional material layer, and
- the second part is in contact with the at least one additional insulating material layer, wherein the first and second parts of the at least one contact point extend parallel to each other, wherein the first part has larger lateral dimensions than the second part and the second part is provided in the form of a contact pad, wherein the second part of the contact point is at least partially surrounded by the additional material layer.

* * * * *